(12) United States Patent
Nelson et al.

(10) Patent No.: US 6,249,708 B1
(45) Date of Patent: Jun. 19, 2001

(54) FLUTED CHANNEL CONSTRUCTION FOR A MULTI-CONDUCTOR CATHETER LEAD

(75) Inventors: Randy S. Nelson, Pine Springs; Roger Dahl, Andover; Duane Zytkovicz, Onamia, all of MN (US)

(73) Assignee: Angeion Corporation, Plymouth, MN (US)

( * ) Notice: Subject to any disclaimer, the term of this patent is extended or adjusted under 35 U.S.C. 154(b) by 0 days.

(21) Appl. No.: 08/918,321

(22) Filed: Aug. 26, 1997

(51) Int. Cl.⁷ ....................................... A61N 1/05
(52) U.S. Cl. .............................................. 607/122
(58) Field of Search ..................... 607/116, 119, 607/122, 123; 600/373, 374, 377, 381

(56) References Cited

U.S. PATENT DOCUMENTS

| | | |
|---|---|---|
| 3,942,536 | 3/1976 | Mirowski et al. . |
| 4,355,646 | 10/1982 | Kallok et al. . |
| 4,559,951 * | 12/1985 | Dahl et al. ........................... 607/122 |
| 4,627,439 | 12/1986 | Harris . |
| 4,630,611 | 12/1986 | King . |
| 4,947,866 | 8/1990 | Lessar et al. . |
| 5,209,229 | 5/1993 | Gilli . |
| 5,325,870 | 7/1994 | Kroll et al. . |
| 5,456,707 | 10/1995 | Giele . |
| 5,545,203 | 8/1996 | Doan . |
| 5,554,178 | 9/1996 | Dahl et al. . |
| 5,571,163 * | 11/1996 | Helland ................................. 607/123 |
| 5,584,873 | 12/1996 | Shoberg et al. . |
| 5,628,778 | 5/1997 | Kruse et al. . |
| 5,676,694 | 10/1997 | Boser et al. . |
| 5,715,817 * | 2/1998 | Stevens-Wright et al. .......... 607/122 |
| 5,746,616 * | 5/1998 | Mar ...................................... 607/122 |
| 5,935,159 * | 8/1999 | Cross, Jr. et al. .................... 607/122 |

FOREIGN PATENT DOCUMENTS

| | | |
|---|---|---|
| WO 94/24931 | 11/1994 | (US) . |
| PCT/US97/ 22706 | 12/1997 | (WO) . |

* cited by examiner

Primary Examiner—George R. Evanisko
(74) Attorney, Agent, or Firm—Patterson, Thuente, Skaar & Christensen, P.A.

(57) ABSTRACT

A multi-conductor fluted channel construction catheter lead is comprised of an elongated flexible tubular inner body member having a peripheral surface on which a plurality of longitudinally-oriented fluted channels are defined. A plurality of elongated conductors are provided with at least one conductor being disposed within one of the fluted channels and operably connected at a distal portion to an electrode and at a proximal portion to a connector. An outer insulative sheath member surrounds the inner body member and the conductors. A method of constructing a fluted channel catheter lead is also disclosed.

17 Claims, 6 Drawing Sheets

FLUTED CHANNEL CONSTRUCTION FOR A MULTI-CONDUCTOR CATHETER LEAD

FIELD OF THE INVENTION

The present invention relates to transvenous catheter electrical leads for use with pacemakers, defibrillators and other tissue stimulating devices. More particularly, the present invention relates to a fluted channel construction for a multi-conductor lead in which the elongated conductors are carried within fluted channels defined around the peripheral surface of an elongated inner body member that is then surrounded by an outer insulative sheath member.

BACKGROUND OF THE INVENTION

Transvenous catheter electrical leads are used with pacemakers, defibrillators and other tissue stimulating devices to deliver electrical stimulation to a desired portion of the body. A transvenous lead is designed to access the desired portion of the body by routing the lead through a vein. The leads are comprised of an elongated tubular body made of a biocompatible, insulative material with one or more elongated conductors inside the lead body. The conductors are connected to an associated electrode located somewhere on the outside of the lead body, either along the body or at the distal end. The conductors are also connected to an associated connector at the proximal end of the lead body. The original transvenous catheter lead for an implantable defibrillator system is described in U.S. Pat. No. 3,942,536 to Mirowski et al.

Typically, a transvenous lead will have more than one electrode and, hence, more than one conductor. While there are numerous ways to construct and attach the electrodes on a multiple conductor lead, the basic construction of existing leads in terms of the arrangement of conductors within the lead can be characterized either as: (1) coaxial, (2) multi-lumen, or some combination of these two constructions. In a coaxial arrangement, each of the conductors is a hollow tube of a different size, with one tube positioned inside the other (i.e., the tubes are coaxial with each other). In a multi-lumen arrangement, each of the conductors is carried in a separate tubular passageway (i.e., lumen) internal to the body of the catheter.

It will be apparent that, as the number of desired conductors is increased, the overall diameter of a transvenous lead increases. In a coaxial arrangement, each new conductor increases the diameter of the lead by at least two times the thickness of the walls of the hollow conductor, as well as the insulation material used to separate the conductors from one another. Examples of coaxial conductor arrangements are shown in U.S. Pat. Nos. 4,355,646, 4,630,611 and 5,456,707 (showing multiple conductors helically wrapped together along a central axis) and U.S. Pat. No. 4,947,866 (showing a center conductor around which a multi-stranded second conductor is wrapped). In a multi-lumen arrangement, the overall increase in the diameter of the lead can sometimes be less than the diameter of the added conductor if the conductors are optimally arranged within the interior space of the insulative lead body. The challenge in increasing the number of conductors in a multi-lumen arrangement is the need for more lumens internal to the lead body countered by the desire to keep the overall diameter of the lead body as small as possible. Examples of multi-lumen conductor arrangements are shown in U.S. Pat. No. 5,209,229 (showing a polyurethane tube catheter lead having one large lumen and two smaller lumens) and U.S. Pat. No. 5,628,778 (showing a quadramulen silicon sleeve used for a single pass lead). U.S. Pat. No. 5,545,203 shows a multilumen lead with additional material surrounding each conductor in the area of the first clavicle rib to serve as a crush resistant protection. A combination of a coaxial and lumen configuration is shown in U.S. Pat. No. 4,627,439 which discloses a pre-shaped polyurethane tube which includes three coiled conductors helically wound around each other within the lumen of an outer coaxial conductor. A different approach to solving the problem of increased conductors and electrodes is taught by U.S. Pat. No. 5,235,870 which discloses a multiplexing arrangement to keep the number of conductors constant while allowing for an increase in the number of electrodes carried by the lead.

While existing techniques for constructing multi-conductor transvenous leads have been acceptable to date because the number of conductors in such leads has been relatively small (e.g., three or less), there is a need for better multi-conductor transvenous leads which can more easily accommodate larger numbers of conductors.

SUMMARY OF THE INVENTION

The present invention is a multi-conductor fluted channel construction catheter lead comprised of an elongated flexible tubular inner body member having a peripheral surface around which a plurality of longitudinally-oriented fluted channels are defined. A plurality of conductors are provided with at least one conductor being disposed within one of the fluted channels and operably connected at a distal portion to an electrode and at a proximal portion to a connector. An outer insulative sheath member surrounds the inner body member and the conductors. A method of constructing a fluted channel catheter lead is also disclosed.

Preferably, the multi-conductor catheter lead has at least one fluted channel which is open to serve either as a crush zone or as a channel for inserting a stiffening material to shape the catheter lead. In the preferred embodiment in which the catheter lead is constructed of a flexible medical grade silicon rubber material, the ability of the fluted channels to serve as mechanisms for inserting a stiffening material to shape the catheter lead provide a significant advantage. Unlike prior catheter leads which were preshaped, the present invention does not require that the polymer material of the body of the catheter lead be a thermoset plastic material, such as polyurethane, in order for the body of the catheter lead to retain a preshaped configuration. Nor does it require that the electrodes and/or conductors be preshaped in order to force the body of the catheter lead into a preshaped configuration. Preferably, a portion of the open channels can be used to create transition zones within the lead whereby any flexing stress on critical areas, such as terminations of the conductor to an electrode, can be longitudinally translated to the edge of the transition zone.

In one embodiment of the present invention, an equal number of open channels and conductor channels are arranged around the peripheral surface of the inner body member. Preferably, the channels are arranged with an equal number of conductor carrying channels and empty channels, and all of the channels are longitudinally spiraled or twisted along the peripheral surface of the inner body member to further reduce stress on the lead conductors. The arrangement and configuration of the channels can take any number of forms. The inner body can also be provided with a center lumen that can contain an additional conductor and serve as a lumen for a stylet. By providing for multiple conductors within the fluted channels of the inner body, the catheter lead also allows for improvements in construction of the lead and connection between the conductors and the electrodes.

In an alternate embodiment of the present invention, a multi-conductor catheter lead includes an elongated flexible tubular inner body member having a plurality of longitudinally-oriented channels defined therein with a plurality of electrodes located along a distal portion of the lead. Each electrode surrounds a portion of the inner body member. A conductor disposed within one of the plurality of channels is operably connected at a distal portion of the conductor to one of the electrodes and at a proximal portion of the conductor to a connector. At least two outer insulative members surround the inner body member, each member surrounding a longitudinal segment of the lead between electrodes. Each outer insulative member abuts at least one of the electrodes and has a radial depth substantially equal to a radial depth of the abutted electrode such that the electrode is flush with an outer surface of the outer insulative member.

The advantages of the fluted channel construction of the catheter lead of the present invention over the existing coaxial or multi-lumen constructions are the increased number of conductors which can be carried by the fluted channel construction, the ability to use empty channels as crush zones, strengthening zones or pre-shaping zones the ability to incorporate transition zones to transfer stress away from fragile termination or joint areas along the lead body, thereby moving any lead stress to more fatigue resistant zones in the lead body, the spiraling of the fluted channels, and hence the conductors carried therein, to emulate the stress resistant characteristics of more conventional coiled conductors, and the ability to create electrodes along the distal portion of the lead which are flush with the surface of the lead body. These advantages allow for construction of smaller diameter catheter leads, and also allow for construction of a single-pass, dual chamber defibrillation lead having at least four conductors and four electrodes which has significant advantages over existing catheter leads

DETAILED DESCRIPTION OF THE PREFERRED EMBODIMENT

Figure 1:
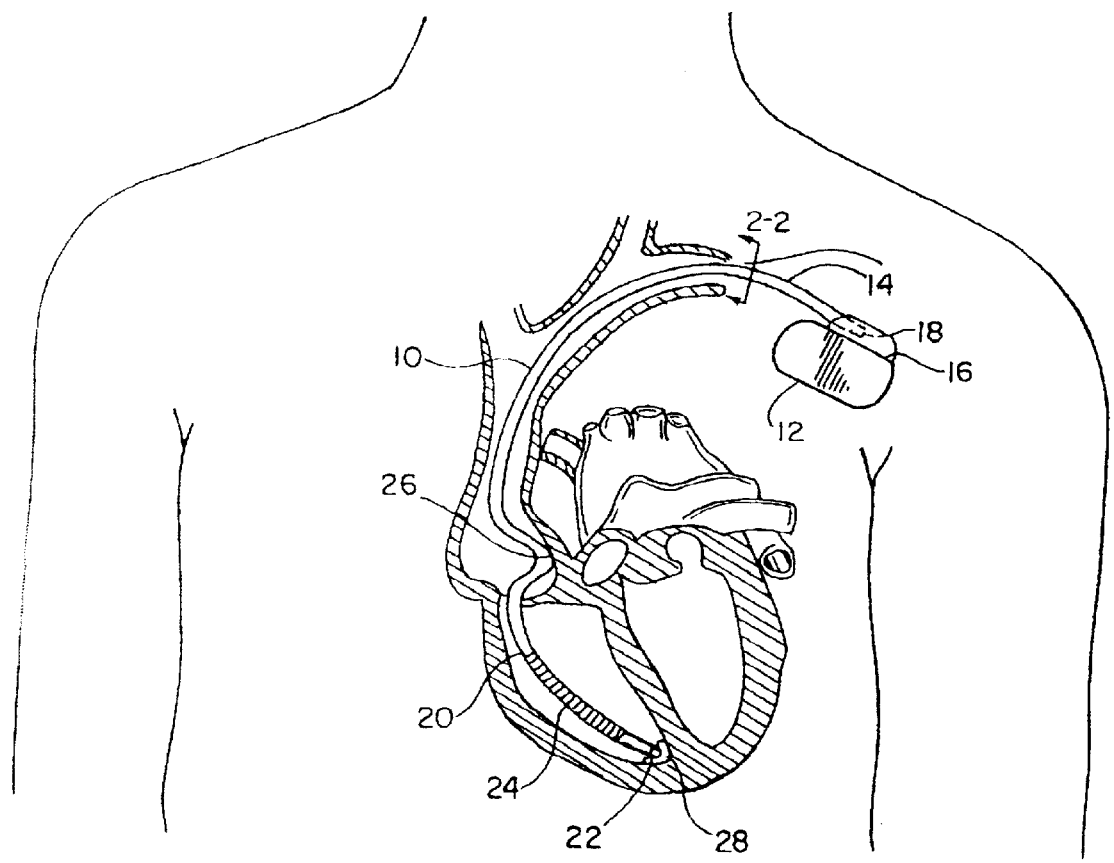
FIG. 1 is a cut-away view showing a preferred embodiment of a catheter lead in accordance with the present invention implanted in a human heart.

Referring to FIG. 1, a multi-conductor catheter lead 10 is shown along with an pulse generator 12 to which a proximal portion 14 of lead 10 is connected, preferably via a header 16 into which a set of connectors 18 are plugged. Located along lead 10 toward a distal portion 20 are electrodes 22, 24 and 26. In this embodiment, electrode 22 is a distal tip pace/sense electrode, electrode 24 is a right ventricular (RV) defibrillation electrode and electrode 26 is an atrial pace/sense electrode pair. Lead 10 is preferably anchored into the apex of the right ventricle by a fixation mechanism 28, such as a set of passive tines or an active helical screw.

Pulse generator 12 is preferably an implantable cardioverter defibrillator which delivers cardioversion/defibrillation electrical countershocks, as well as pacing pulses, to either or both of the atrial and ventricular chambers of the heart. Alternatively, implantable pulse generator 12 may be a pacemaker, nerve stimulator or other similar implantable device capable of generating an electrical stimulation to be delivered to a human patient via catheter lead 10.

Figure 2:
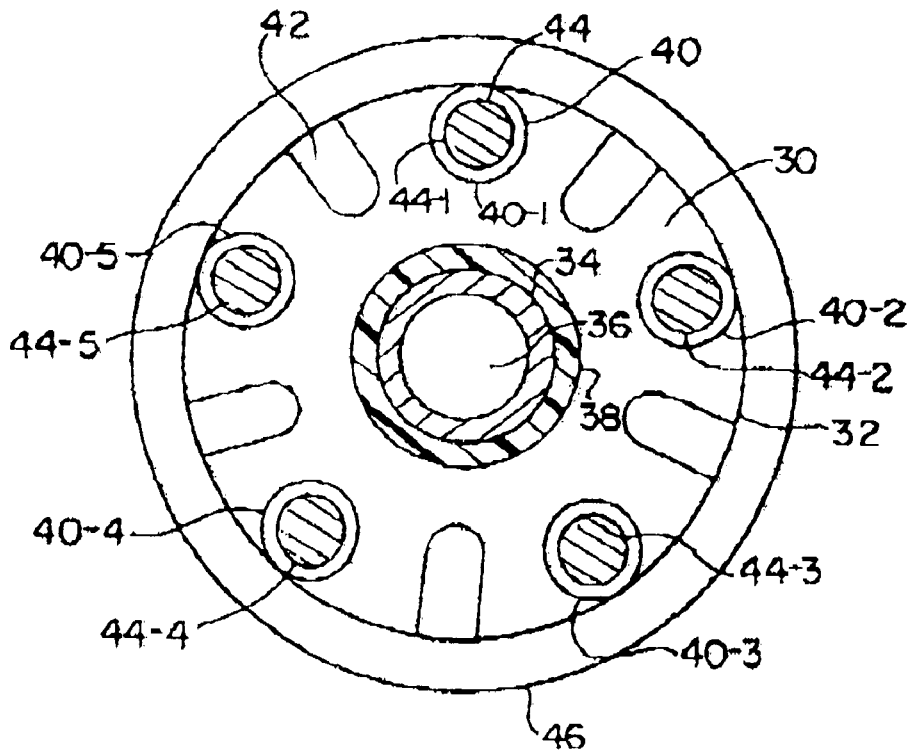
FIG. 2 is a transverse cross-sectional view of the catheter lead along lines 2—2 of FIG. 1.

FIG. 2 is cross sectional view of catheter lead 10 taken along lines 2—2 of FIG. 1. As shown in FIG. 2, catheter lead 10 is preferably comprised of an elongated flexible insulative inner body member 30 having a peripheral surface 32. In this embodiment, inner body member 30 is tubular and is adapted to receive a central coil conductor 34 which extends the length of catheter lead 10 and connects at distal end 20 to electrode 22. In this way, inner body member 30 and central coil conductor 34 define a central lumen 36 through which a stylet (not shown) may be inserted for controlling the placement and orientation of catheter lead 10 during implantation. It will be understood that, in addition to serving as a conductor for electrode 22, central coil conductor 34 also serves to protect inner body member 30 from punctures and aids in allowing the stylet to slide freely in central lumen 36 as catheter lead 10 is positioned. Preferably, a non-conductive tubular stiffening sheath 38, such as polytetraflouroethylene (PTFE) tubing, is interposed between inner body member 30 and central coil conductor 34 to further reinforce the assembly. If central coil conductor 34 is eliminated, tubular stiffening sheath 38 could serve as the protective channel for the stylet. Alternatively, if an exterior catheter sheath or the like is used to control the placement and orientation of catheter lead 10 during implantation, the need for central lumen 36 is eliminated, and inner body member 30 may be solid rather than tubular. In the preferred embodiment, the outside diameter of catheter lead is about 10 French, although it will be recognized that due to the advantages of the fluted channel construction of the present invention, this diameter can be further decreased in the alternate embodiments and still provide an effective multi-conductor catheter lead, particularly a multi-conductor catheter lead having more than 3–4 conductors.

Unlike existing catheter leads which are either coaxial or multi-lumen, a plurality of longitudinally-oriented fluted channels 40, 42 are defined around the peripheral surface 32 of body member 30. In this embodiment, each of the fluted channels 40 carries at least one conductor 44 within the channel 40 and each of the fluted channels 42 does not have a conductor within the channel 42. Each conductor 44-1, 44-2, 44-3, 44-4 and 44-5 is disposed within a corresponding one of the fluted channels 40-1, 40-2, 40-3, 40-4 and 40-5 and is operably connected at a distal portion to one of the electrodes 22, 24 or 26 and at a proximal portion to one of the set of connectors 18. An outer insulative sheath member 46 surrounds the inner body member 30 and the conductors 44. Outer sheath member 46 is preferably comprised of multiple segments, each segment to be positioned between electrodes electrodes 22 and 24, electrodes 24 and 26-1, electrodes 26-1 and 26-2 and electrodes 26-2 and the connectors 18. Preferably, sheath member 46 has a radial depth which is selected to match a radial depth of the RV electrode 24, such that RV electrode 24 is substantially flush with the surface of the adjacent sheath member 46. The ability to create a flush electrode/lead interface, instead of overmolding the lead around the ends of the electrode, has advantages in reducing the effective diameter of the lead 10. In addition, for the RV electrode 24, the arrangement described herein reduces the chances of damage to the bicuspid valve when the lead 10 is passed into the ventricular chamber.

Figure 3:
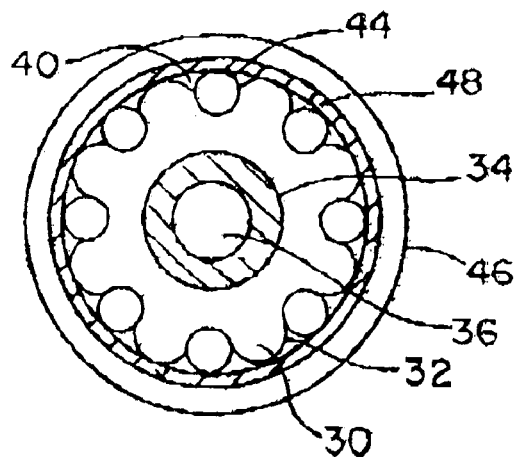
FIG. 3 is a transverse cross-sectional view of an alternate embodiment of the catheter lead of FIG. 2.

As shown in FIG. 3, an optional tubular stiffening sheath 48 can be interposed between inner body member 30 and outer sheath member 46 to provide additional structural strength and insulation value instead of, or in addition to, stiffening sheath 38. Stiffening sheath 48 can also aid in allowing inner body member 30 to be strung into outer sheath member 46. FIG. 3 also shows an embodiment of the present invention in which all of the fluted channels 40 carry conductors 44 and there are no empty channels 42. In one embodiment, the insulative outer sheath member 46 is transparent and each of the conductors 44 may be provided with a uniquely colored insulation coating to facilitate identification and assembly of the lead.

Preferably, inner body member 30 and outer sheath member 46 are both made of medical grade silicone rubber, although different materials can be used for either or both members. The outer insulative member 46 may be selected from the set consisting of: a tubular sheath of material the same as a material of the inner body member 30, a tubular sheath of material different from the material of the inner body member30, a material the same as the material of the inner body member which is overmolded over the inner body member 30 and the conductors 44, and a material different from the material of the inner body member 30 which is overmolded over the inner body member 30 and the conductors 44.

Figure 6:
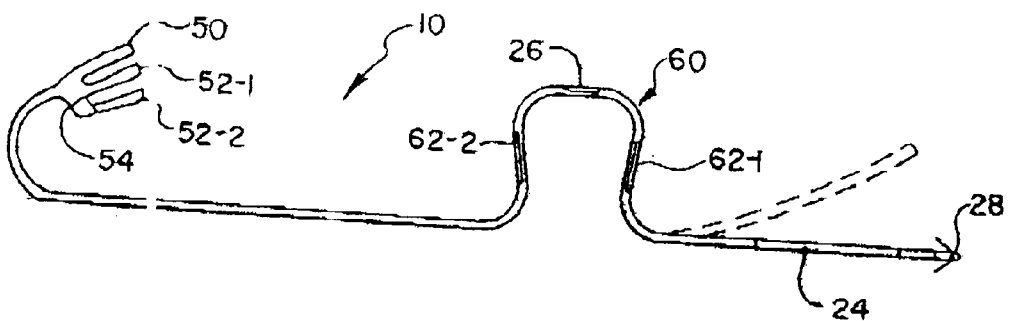
FIG. 6 is a plan view of the distal portion of the catheter lead of FIG. 1.

Preferably, each conductor 44 is a multifilar wound coil, although a unifilarwound coil, a multifilament cable, or any combination thereof could be used for the conductors 44. Although only one conductor 44 per channel 40 is shown, it is also possible to provide mulitple conductors 44 within a single channel 40, depending upon the size of the conductors and the size of the channel. Preferably, electrode 22 is a tip electrode, electrode 24 is a coil defibrillation electrode, and electrode 26 is a pair of surface projection electrodes. Alternatively, electrodes 22, 24 and 26 could be a tubular defibrillation electrode, a ring electrode, a mesh electrode, or any combination thereof. Preferably, the set of connectors 18 consists of a standardized DF-1 defibrillation connector pin 50 and two standardized IS-1 pace/sense connector pins 52-1, 52-2 extending from a yoke 54 near the end of the proximal portion 14 of catheter lead 10 as shown in FIG. 6. It will be recognized, however, that numerous variations of conductor-to-electrode and conductor-to-connector connections can be accomplished with the present invention including: a single conductor connected to a single electrode and a single connector, a single conductor connected to multiple electrodes and a single connector, multiple conductors connected to a single electrode and a single connector, multiple conductors connected to a single electrode and multiple connectors, or multiple conductors connected to multiple electrodes and a single connector.

As shown in FIG. 2, the fluted channels 40 are constructed having a transverse cross-sectional area that is generally circular and corresponds to a cross-sectional area of conductors 46 so as to seat and retain the conductors within the respective channels. Preferably, the portion of the circular cross-sectional area of fluted channel 40 which is open to the peripheral surface 32 of inner body member 30 is less than 180 degrees so as to provide for a pair of protrusions that assist in retaining the conductor 46 within the fluted channel 40. Alternatively, channels 40 and 42 could be extruded with a thin piece of material remaining over the intended opening of the channel so that there would be no opening. In this situation, the thin piece of material would be slit prior to insertion of the associated conductors 44 or the insertion of a stiffening material.

Fluted channels 42 are constructed having a transverse cross-sectional area that is generally U-shaped. This shape allows for easy insertion of molding materials as will be described, and also serves as a crush zone area to allow for deformation of catheter lead 10 in response to external forces, such as the forces exerted between the ribs and the clavicle when catheter lead 10 is inserted in the subclavian or subphalic vein. In addition, by having multiple channels 42 uniformly radially spaced around the peripheral surface 32 of inner body member 30, the deformation characteristics of catheter lead 10 are uniformly enhanced in all orientations. The fact that material is removed from within inner body member 30 to create fluted channel 42 also enhances the flexibility of catheter lead 10, thereby enhancing ease of implantation and overall chronic performance of the implanted lead 10 within the body.

Figure 4:
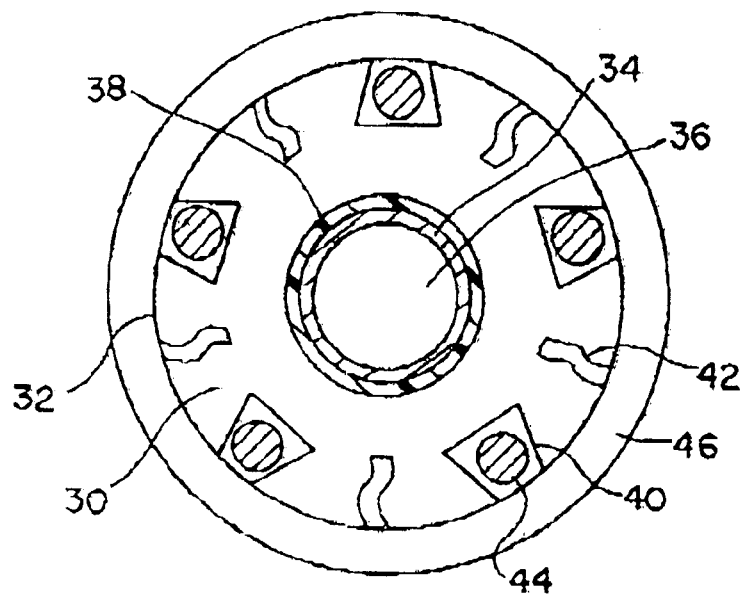
FIG. 4 is a transverse cross-sectional view of another alternate embodiment of the catheter lead of FIG. 2.
Figure 5:
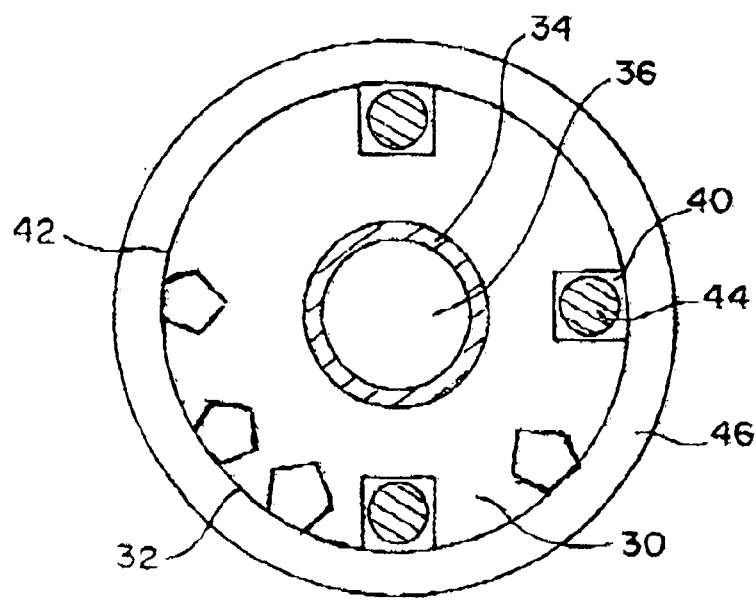
FIG. 5 is a transverse cross-sectional view of another alternate embodiment of the catheter lead of FIG. 2.

FIGS. 4 and 5 show alternate transverse cross-sectional constructions of catheter lead 10 that provide for a generally triangular cross-sectional area and a generally trapezoidal cross-sectional area, respectively, for the shape of fluted channels 40. While these shapes do not generally conform to the cross-sectional shape of conductors 44, these shapes do provide for additional deformation space within the construction of catheter lead 10. Fluted channels 42 are shown as having a generally sigmoi-dal shaped cross-sectional area and a generally diamond-shaped cross-sectional area, respectively. In FIG. 5, fluted channels 40 and 42 are non-uniformly radially spaced around the peripheral surface 32 of inner body member 30. It will be noted that such non-uniform radially spacing can occur throughout the length of catheter lead 10, or can be caused to occur only in selected longitudinal portions of the lead to assist in the pre-shaping or configuration of that portion of catheter lead 10. It will also be noted, as shown in FIG. 4, for example, that not all of the fluted channels 42 need be of uniform cross-sectional size. Similarly, the cross-sectional size or shape does not necessarily need to be uniform throughout the longitudinal length of catheter lead 10.

Figure 8:
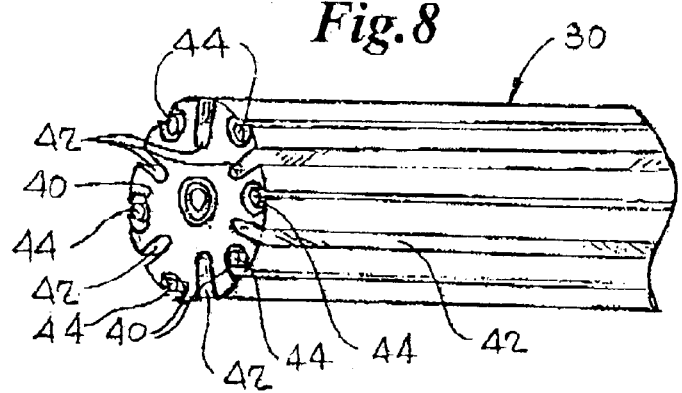
FIG. 8 is an isometric view of a segment of the catheter lead of FIG. 6 without the outer layer.
Figure 9:
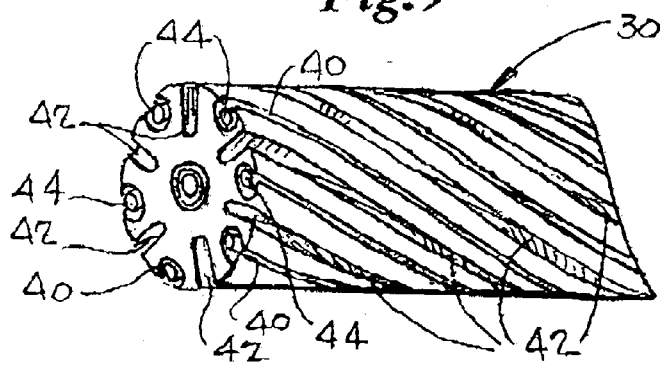
FIG. 9 is an isometric view of a segment of an alternate embodiment of the catheter lead without the outer layer.

Generally, each of the longitudinally-oriented fluted channels 40, 42 will extend from the proximal end 14 to at least a distal portion 20 of catheter lead 10. As shown in FIG. 8, each of the fluted channels 40, 42 extend in a longitudinally spiraled configuration with the conductors 44 also assuming the longitudinally spiraled configuration from the proximal end 14 to the distal portion 20, just proximal to the connection with the tip electrode 22. In an alternate embodiment as shown in FIG. 9, the fluted channels 40, 42 are disposed in a longitudinally straight configuration and one or more of the longitudinally fluted channels 40, 42 is discontinued prior to the distal portion 20 of catheter lead 10.

In a preferred embodiment as shown in FIG. 6, catheter lead 10 is preshaped in an atrial portion 60 corresponding to the atrial chamber of the heart when a distal tip 28 is disposed in the ventricular chamber of the heart. The distance from the distal tip 28 to the atrial portion 60 can be of varying lengths to accommodate different size hearts. In a preferred embodiment, catheter lead 10 is provided in a set of lengths corresponding to different distances between distal tip 28 and atrial electrode 26 for different size hearts. This preshaped atrial portion 60 is preferably U-shaped and includes a pair of atrial fixation sites 62-1, 62-2 located within atrial portion 60 but longitudinally spaced from atrial electrode 26. The atrial fixation sites 62 are utilized to secure the preshaped portion 60 to the atrial wall at a location other than atrial electrode 26, thereby providing strain relief for atrial electrode 26 to enhance the electrode/tissue interface and improve chronic pacing performance. For a more detailed description of a preferred embodiment of the atrial fixation sites 62, reference is made to the co-pending application entitled "CATHETER LEAD WITH REMOTE ATRIAL FIXATION SITES", Ser. No. 08/729,900, filed Oct. 15,1996, which is hereby incorporated by reference.

Figure 7:
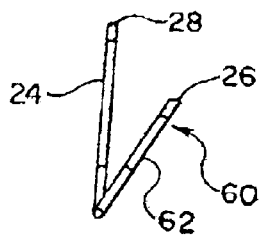
FIG. 7 is an end view of the distal portion of the catheter lead of FIG. 6 showing the canting of the atrial electrodes.

As shown in FIG. 7, the preshaped atrial portion 60 is also canted relative to the distal portion 20 which is disposed in the ventricular chamber of the heart. Distal portion 20 is also preferably preshaped or flexible in an orientation as shown in FIG. 6 which allows distal portion 20 to assume a curved configuration in a plane corresponding to a lateral cross section of the heart. In contrast, preshaped atrial portion 60 is preshaped in an orientation which extends out of the plane corresponding to a lateral cross section of the heart.

Referring now to FIGS. 10–13, the assembly of a preferred embodiment of the catheter lead 10 will now be described. The general approach is to assemble the catheter lead 10 from the distal tip 28, performing all of the high risk assembly operations before stringing the conductors 44. In this way, if a high risk assembly operation fails, the value of the conductors and electrodes may not be wasted.

Figure 10A:
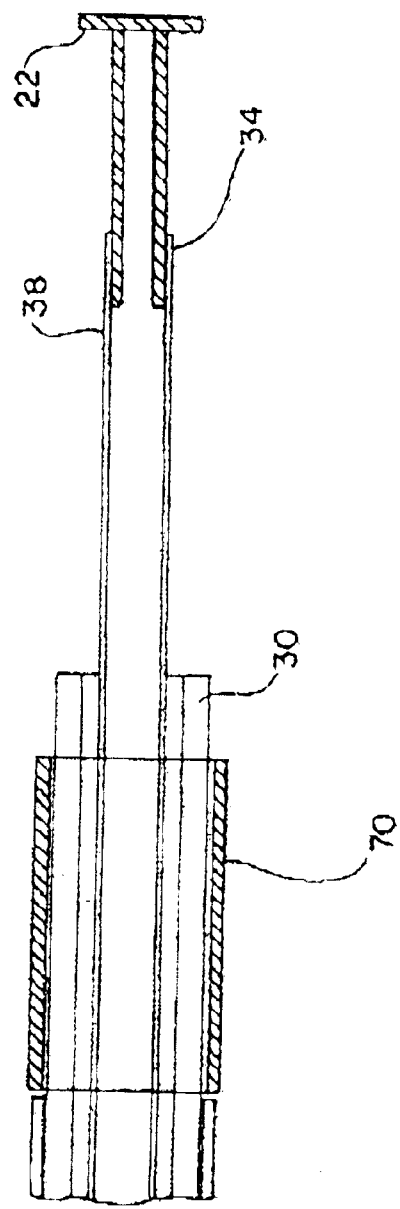
FIG. 10 is a longitudinal cross-sectional view of the distal portion of the catheter lead of FIG. 1 showing the RV shocking electrode assembly.
Figure 10B:
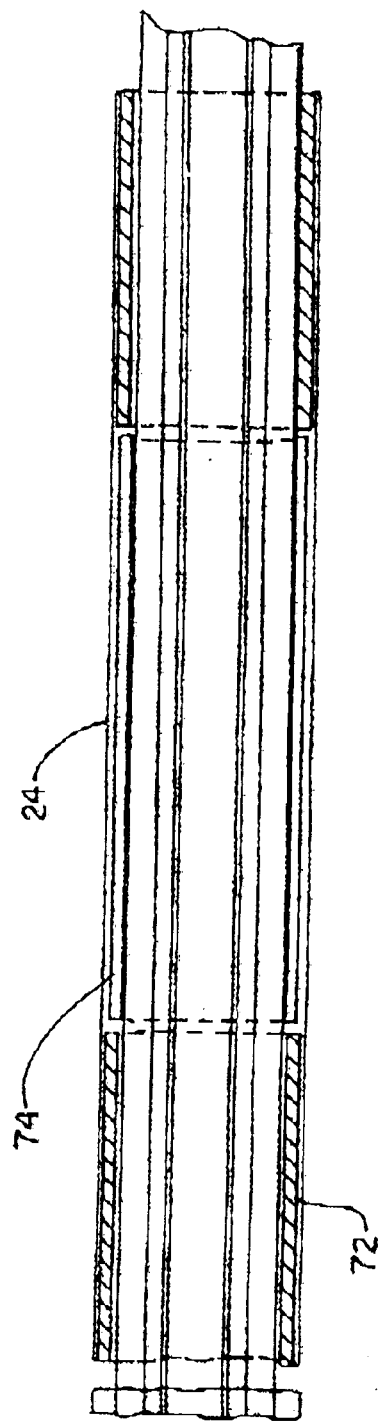

As shown in FIG. 10, the central coil conductor 34 is spot welded to the tip electrode 22. This requires the inner coil 34 to be expanded and worked onto the shank of the pacing tip 22. Depending on the design of the premolded tine section 28, it may be possible to incorporate a crimp joint. Alternatively, the fixation section 28 could incorporate an active fixation tip that was or was not electrically connected to the pacing tip 22. The PTFE tubing 38 is heat shrunk onto the inner coil 34, preferably over lapping a portion of the shank of the pacing tip 22. The fluted tubing 30 is string onto the inner coil 34.

To connect the three conductors 44 to the RV shocking electrode 24 in the preferred embodiment, the DBS conductors 44 for the RV shocking electrode 24 are stripped at their distal ends using a laser or alcohol torch. Two of the DBS conductors 44-1 and 44-2 are allocated for the distal termination to the RV shocking electrode 24 and are welded to a distal RV terminal ring 70. Alternatively, the two DBS conductors 44 are crimped into a hypodermic tubing and welded to the inner diameter of the distal terminal ring 70. Similarly, the single DBS cable 44-3 allocated for the proximal termination to the RV shocking is welded to a proximal RV terminal ring 72. These welds are preferably laser welds which are subsequently stress stabilized with medical adhesive. Alternatively, these joints could be formed by a mechanical crimp, a laser weld, a resistance weld, or any combination thereof. The RV shocking electrode 24 is strung over a segment silicone rubber support tubing 74 that is positioned between the distal terminal ring 70 and the proximal terminal ring 72. The support tubing 74 is of the same thickness as the rings 70, 72 to provide a uniform outer diameter over which the shocking electrode 24 is strung. The distal end of the RV shocking electrode 24 is welded to the distal RV terminal ring 70. The proximal terminal ring 72 is also welded to the RV shocking electrode. Depending upon the configuration of the channels 40, fixturing may be necessary to circumferencially align and retain the various DBS cables 44 with the channels 40 in the fluted tubing 30 during this process.

Figure 11:
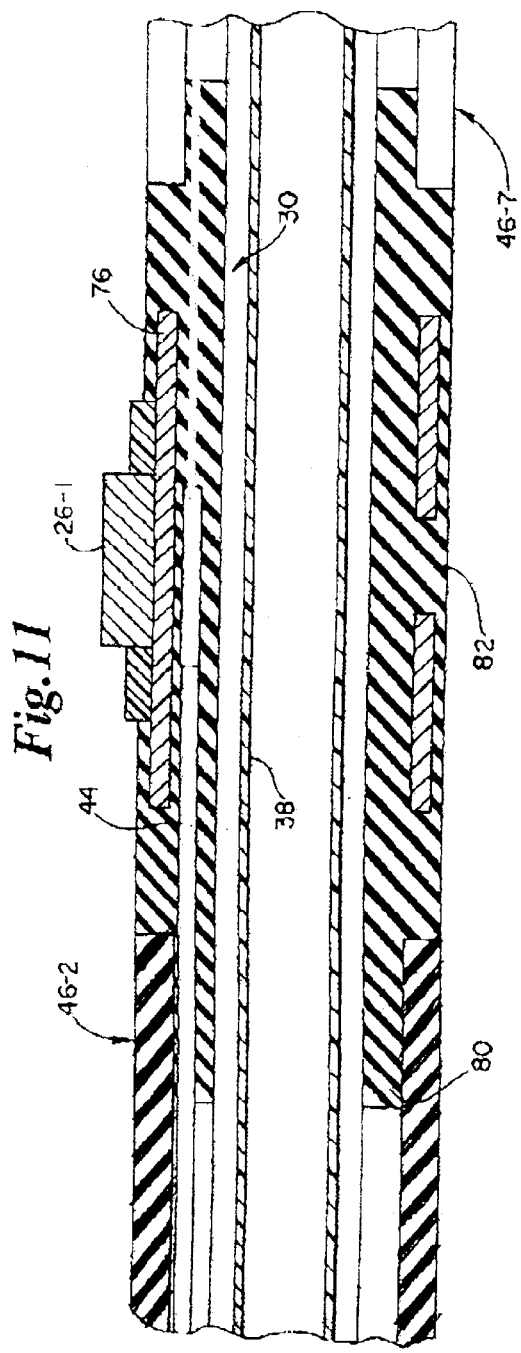
FIG. 11 is a longitudinal cross-sectional view of the atrial portion of the catheter lead of FIG. 1 showing the atrial electrode assembly.
Figure 12:
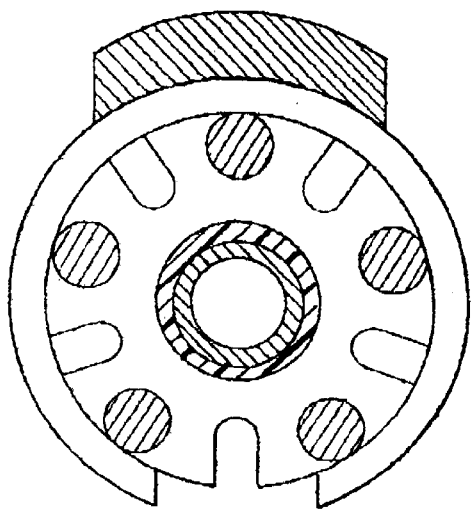
FIG. 12 is a transverse cross-sectional view of an atrial electrode as shown in FIG. 11.

As shown in FIGS. 11 and 12, the two atrial conductors 44 are welded to the inner diameter of a termination ring 76 for each of the atrial electrodes 26-1 and 26-2. These welds are preferably laser welds which are subsequently stress stabilized with medical adhesive. Unlike RV electrode 24, atrial electrodes 26-1 and 26-2 are preferably formed of a porous material which is constructed so as to extend above the surface of outer silicon tubing 46. In this way, atrial electrodes are more likely to encourage the fibrosis in the atrium necessary for stabilizing the electrode/tissue interface.

As the various electrodes 24, 26 are strung onto the fluted tubing 30, pieces of the outer tubing 46-1, 46-2 which are cut to length will be applied over the fluted tubing 30. The pre-molded tine section 28 is then bonded to the tip assembly 22 leaving a small gap between the proximal end of the premolded tines 28 and the distal end of the RV shocking electrode 24. This gap is molded with liquid silicone rubber to secure the premolded tines 28 to the catheter lead 10, thereby creating a transition zone. The liquid silicone rubber preferably is forced into the channels 42 of the fluted tubing 30 and under the distal RV terminal ring 70 under pressure. One alternative to the pressure insertion of the liquid silicone rubber is to pre-pack these areas with either gum stock or liquid rubber prior to assembly. It will be recognized that, depending upon the materials used for the body of the catheter lead 10, other alternatives for stiffening/shaping materials could be used such as other liquid or B-stage polymers, glues or a flexible rod-like stiffeners/shapers such as preformed metal or plastic rods or the like. The principal feature of the stiffening/preshaping material is that it has a modulus of elasticity which is less than a modulus of elasticity of the material used for the body of the catheter lead 10 such that the stiffening/preshaping material creates an effective transition zone along the length of the lead in the area of the stiffening/preshaping material. Preferably, the transition zone is used to translate any stress forces that could cause fatigue away from sensitive portions of the lead body, such as conductor/electrode termination points or other similar joint areas.

The same technique used for securing the premolded tines 28 is also used to mold the atrial portion 60 adjacent to the atrial electrodes 26. Locating pins (not shown) are incorporated into a preshaped mold (not shown) into which the lead 10 is placed. The locating pins mate with the locating holes 82 to position the atrial electrodes 26 during molding. Liquid silicone rubber is then inserted under pressure into the open channels 42 surrounding the atrial electrodes to increase the stiffness of the catheter lead 10 in the region of the atrial electrodes, thereby creating a transition zone as shown at 80. After the liquid silicone rubber has cured, the finished catheter lead 10 is removed from the mold. Any small gaps left in the outer diameter of the molded lead assembly from these molding pins can be filled with medical adhesive.

The preshaped mold preferably incorporates the compound curves of the preferred shaped of atrial portion 60 of the catheter lead 10 as described above to form the curved sections of the lead. Small sections of the outer tubing 46 can be omitted to facilitate molding of the outer portion of the lead body in these curved sections. It is important to get good penetration of the molded rubber into the fluted tubing channels 42, in order to create the desired transition zones. As previously indicated, the molding of the preshaped zones may require some fixturing to insure proper alignment of the various electrodes and curves. In addition, the preshaped mold can also incorporate a preferred curve of a ventricular portion of the catheter lead 10 between the atrial portion 60 and the tip electrode 22 such that the ventricular portion forms a curved portion conforming generally to the interior curve of the ventricular chamber. Because the catheter lead 10 is preferably constructed of a flexible medical grade silicon rubber material, the ability of the fluted channels 42 to serve as mechanisms for inserting a stiffening material to shape the catheter lead provide allows for the construction of either or both transition zones (i.e., longitudinal lengths of the lead having different flexibility characteristics than adjacent regions) and preshaped zones (i.e., longitudinal lengths of the lead which are preshaped other than in a straight orientation).

As shown in FIG. 11, a temporary PTFE washer 84 around the atrial electrode 26 can be used to prevent liquid silicone rubber from being injected into these porous electrodes 26. These washers 84 are removed after post curing. These washers 84 may be in the form of a small cap that fits over the electrodes 26 more completely sealing them from contamination. A PTFE shrink tubing (not shown) over the RV shocking electrode 24 can be used to seal against rubber ingress into the shocking electrode coil during the molding process. This requires the mold to clamp down on the PTFE tubing to insure a good seal.

Figure 13:
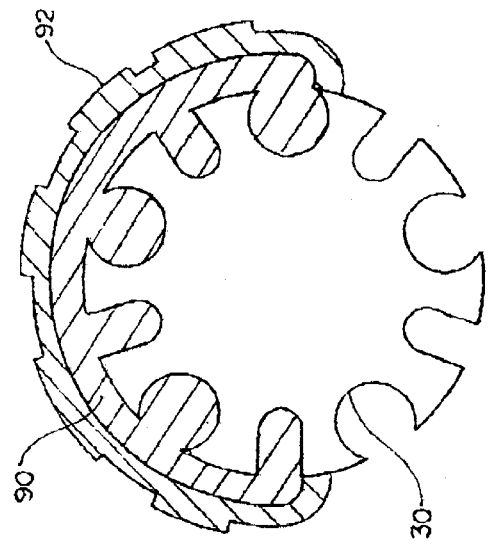
FIG. 13 is a transverse cross-sectional view of an atrial anchoring location as shown in FIG. 11.

Referring now to FIG. 13, the formation of the various anchoring sites 62 remote to the atrial electrodes 26 will be described. Preferably, anchoring sites 62 are based on exposed dacron patches bracketing the atrial electrodes 26. In addition to the nature of the anchoring material, there are several additional ways of accelerating the fibrotic tissue growth at the anchoring site, including: use of a knurled substrate, use of Albumin, and gel foam or other homeostatic agents. The fixation sites 62 are fabricated in a multi step process. First, a support section 90 is molded onto the fluted tubing 30. The exterior portion of the support section 90 (i.e., the area under the dacron windows) is preferably knurled. Next, a mesh material 92, such as dacron, is positioned on the support surface 90. Preferably, the mesh material 90 is impregnated with some fixation accelerating agent. The outer surface of the fixation section of the lead is then molded in the manner described above to incorporate any transition or preshaped zones as desired. During this molding process, windows will be provided in this outer molding to expose the mesh material 92.

We claim:

1. A multi-conductor catheter lead comprising:
   an elongated flexible tubular inner body member having a peripheral surface around which are defined a plurality of longitudinally-oriented fluted channels;
   a plurality of elongated conductors, at least one electrode and at least one connector, at least one of the conductors being disposed within at least one of the plurality of fluted channels and each conductor operably connected at a distal portion of the conductor to an electrode and at a proximal portion of the conductor to a connector;
   a stiffening material filling at least a portion of at least one of the plurality of longitudinally-oriented fluted channels that is open and without a conductor such that the stiffening material generally shapes the catheter lead along a length of the catheter lead corresponding to the portion which is filled; and
   an outer insulative member surrounding the inner body member and the conductors.

2. The catheter lead of claim 1 wherein the fluted channels are constructed having a longitudinal cross-sectional area selected from one or more of the group consisting of: a generally semi-circular cross-sectional area, a generally circular cross-sectional area, a generally triangular cross-sectional area, a generally trapezoidal cross-sectional area, a generally U-shaped cross-sectional area, a generally sigmoidal-shaped cross-sectional area or any combination thereof.

3. The catheter lead of claim 1 the wherein fluted channels are oriented relative to one another in a manner selected from the group consisting of: uniformly radially spaced and longitudinally straight, non-uniformly radially spaced and longitudinally straight, uniformly radially spaced and longitudinally spiraled, non-uniformly radially spaced and longitudinally spiraled.

4. The catheter lead of claim 1 wherein the conductors are selected from the group consisting of: a multifilar wound coil, a unifilar wound coil, a multifilament cable, or any combination thereof.

5. The catheter lead of claim 1 wherein the at least one electrode is selected from the group consisting of: a coil defibrillation electrode, a tubular defibrillation electrode, a ring electrode, a surface projection electrode, a tip electrode, a mesh electrode, or any combination thereof.

6. The catheter lead of claim 1 wherein the conductors are connected to the at least one electrode by a mechanical/electrical connection selected from the set consisting of: a mechanical crimp, a laser weld, a resistance weld, or any combination thereof.

7. The catheter lead of claim 1 wherein the connections between the conductors, the at least one electrode and the at least one connector are selected from the group consisting of: a single conductor connected to a single electrode and a single connector, a single conductor connected to multiple electrodes and a single connector, multiple conductors connected to a single electrode and a single connector, multiple conductors connected to a single electrode and multiple connectors, or multiple conductors connected to multiple electrodes and a single connector.

8. The catheter lead of claim 1 wherein the inner body member has a lumen defined therein.

9. The catheter lead of claim 8 further comprising a coiled tubular conductor disposed within the lumen of the inner body member, the tubular conductor having a lumen defined therein for receiving a stylet.

10. The catheter lead of claim 1 wherein the inner body member and the outer insulative member are comprised of a medical grade silicone rubber.

11. The catheter lead of claim 1 wherein the outer insulative member is selected from the group consisting of: a tubular sheath of material the same as a material of the inner body member, a tubular sheath of material different from the material of the inner body member, a material the same as the material of the inner body member which is overmolded over the inner body member and the conductors, and a material different from the material of the inner body member which is overmolded over the inner body member and the conductors.

12. The catheter lead of claim 1 wherein at least one of the fluted channels extends for only a portion of the longitudinal length of the catheter lead.

13. The catheter lead of claim 1 wherein there are at least four conductors and at least four electrodes, including: a tip electrode, a defibrillation electrode, and two atrial electrodes.

14. The catheter lead of claim 1 wherein the insulative outer sheath member is transparent and wherein each of the plurality of conductors is provided with a uniquely colored insulation coating.

15. The catheter lead of claim 1 wherein one of the electrodes is a defibrillation electrode and multiple of the conductors are connected to the defibrillation electrode at separate locations along the defibrillation electrode.

16. The catheter lead of claim 15 wherein the multiple conductors connected to the defibrillation electrode are comprised of drawn brazed stranded (DBS) cable.

17. The catheter lead of claim 15 wherein at least two conductors are connected to a distal termination of the defibrillation electrode and at least one conductor is connected to a proximal termination of the defibrillation electrode.

\* \* \* \* \*